United States Patent [19]
Walch et al.

[11] Patent Number: 5,614,491
[45] Date of Patent: Mar. 25, 1997

[54] LIQUID PREPARATIONS CONTAINING CYCLOSPORIN AND PROCESS FOR PREPARING SAME

[75] Inventors: Hatto Walch, Laupheim - Baustetten; Monika Fleck, Laupheim; Klaus Neuer, Grossschafhausen, all of Germany

[73] Assignee: Dr. Rentschler Arzneimittel GmbH & Co., Laupheim, Germany

[21] Appl. No.: 347,289

[22] Filed: Nov. 30, 1994

[51] Int. Cl.⁶ .......................... A61K 38/00; A61K 47/14
[52] U.S. Cl. .................................... 514/11; 514/9
[58] Field of Search ............................ 514/9, 11

[56] References Cited

U.S. PATENT DOCUMENTS

| | | |
|---|---|---|
| 4,388,307 | 6/1983 | Cavanak . |
| 4,803,081 | 2/1989 | Falk et al. .................. 424/888 |
| 5,206,219 | 4/1993 | Desai .......................... 514/3 |

FOREIGN PATENT DOCUMENTS

| | | |
|---|---|---|
| 0539319A2 | 4/1993 | European Pat. Off. . |
| 0589843A1 | 3/1994 | European Pat. Off. . |
| 3924207 | 1/1990 | Germany . |
| 641356 | 2/1984 | Switzerland . |
| 2222770 | 3/1990 | United Kingdom . |
| 2228198 | 8/1990 | United Kingdom . |
| 2230440 | 10/1990 | United Kingdom . |
| WO92/09299 | 6/1992 | WIPO . |

*Primary Examiner*—Howard E. Schain
*Assistant Examiner*—P. Lynn Touzeau
*Attorney, Agent, or Firm*—Ratner & Prestia

[57] ABSTRACT

The present invention pertains to cyclosporin-containing liquid preparations for oral or parenteral administration, as well as to a process for preparing same. Besides the active ingredient cyclosporin, the preparations contain a polyoxyethylene glycerol fatty acid monoester and a monohydric and/or polyhydric alcohol(s). The preparations are stable and well tolerated, and they have higher bioavailability than the preparations known currently.

13 Claims, No Drawings

LIQUID PREPARATIONS CONTAINING CYCLOSPORIN AND PROCESS FOR PREPARING SAME

FIELD OF THE INVENTION

The present invention pertains to liquid preparations containing cyclosporin, especially cyclosporin A, for oral or parenteral administration, and to a process for preparing same.

BACKGROUND OF THE INVENTION

Cyclosporins are cyclic oligopeptides of microbiological origin, which are used especially as immunosuppressives.

Cyclosporins, especially cyclosporin A, are used in connection with organ transplantation to prevent the rejection of the transplanted organ.

It has also been known that cyclosporins have antiinflammatory and antiparasitic actions.

Therefore, the use of cyclosporins is not limited to immunosuppressives, but it also includes various autoimmune diseases and inflammatory conditions, especially inflammatory conditions in which autoimmune processes are involved. They include arthritic diseases, e.g., rheumatoid arthritis and rheumatic diseases.

Cyclosporins can be used as antiparasitic agents for the treatment of protozoal infections, e.g., malaria.

However, severe side effects, especially nephrotoxic effects, must be accepted with the cyclosporin formulations currently used in practice.

Cyclosporins are substances of a highly hydrophobic nature. Due to their poor solubility in water, it is difficult to process cyclosporins with the usual pharmaceutical carriers to prepare preparations of sufficient bioavailability.

The cyclosporin-containing pharmaceutical preparations disclosed in the prior art are based on the use of an alcohol and/or oils or similar vehicles in conjunction with a surface-active agent.

U.S. Pat. No. 4,388,307 discloses the solution of cyclosporin in a mixture of transesterification products of various oils formed with polyethylene glycol (e.g., Labrafil M 1499 CS a product of Gattefosse, France), as well as ethanol and a vegetable oil. However, the products thus obtained are unsuitable for intravenous administration because they contain oil. They can be administered only subcutaneously or intramuscularly.

According to product information on the Sandimmun drinking solution sold by Sandoz Pharmeceutical (Chapter XII, Sandoz-Pharma, Basel, 1984), cyclosporin is dissolved in a solution of polyoxyethylated castor oil (e.g., Cremophor EL, available from BASF) and ethanol. The disadvantage of these preparations is the fact that they are poorly tolerated by the patients, because anaphylactic reactions frequently develop (KAHAN et al., Lancet, 1984, I:52; LEUNISSEN, K. M. et al., Lancet, 1985, I:636).

PCT Application WO 92/09299 discloses oral liquid pharmaceutical preparations which contain a cyclosporin in a mixture of a hydrophilic solvent and a surface-active agent. Polyoxyethylene-polyoxypropylene block polymers (polyoxamers) with molecular weights of 1,000 to 15,500 are used as surface-active agents. The disadvantage of this formulation is the precipitation of the active ingredient in contact with aqueous solutions. These formulations are unsuitable for parenteral administration because of the solubilizing ability of the polyoxamers.

SUMMARY OF THE INVENTION

The goal of the present invention is to provide liquid preparations containing cyclosporin or cyclosporins, which are poorly soluble or insoluble in water, which can be diluted with water in any quantity ratio and form clear, stable solutions.

Another goal of the present invention is to provide formulations which lead to better bioavailability of the active ingredient and thus make it possible to reduce the amount of active ingredient to be administered.

The applicant has surprisingly found that the above-described goals can be accomplished with a solution which contains cyclosporin dissolved in a mixture of a nonionics emulsifying agent such as polyoxyethylene glycerol fatty acid monoester and monohydric and/or polyhydric alcohols, wherein the solutions are stable, well tolerated, have improved bioavailability, and can be administered either orally or parenterally.

More specifically, the present invention pertains to liquid pharmaceutical preparations for oral or parenteral administration, which contain cyclosporin as the active ingredient in combination with a polyoxyethylene glycerol fatty acid monoester and monohydric and/or polyhydric alcohol(s).

DETAILED DESCRIPTION OF THE INVENTION

Polyoxyethylene glycerol fatty acid monoesters (PGFME) are nonionic emulsifying agents, especially those commercially available under the name Tagat from Th. Goldschmidt AG, Germany. Preferred compounds among them are the monoesters of lauric, stearic, oleic and isostearic acids. Especially preferred are the monoesters of oleic acid and lauric acid, which are commercially available under the names Tagat O and Tagat L. The HLB value of the emulsifying agent used is in the range of 10 to 20 and preferably 14 to 17.

The solution concentrations according to the present invention contain 1 to 20 parts by weight of PGFME and 0.5 to 20 parts by weight of the monohydric and/or polyhydric alcohols, preferably 10 to 20 parts PGFME and 2 to 10 parts alcohol and especially 12 to 18 parts of PGFME and 3 to 6 parts of alcohol relative to one part by weight of active ingredient.

All the known natural and synthetic cyclosporins, including their analogs and derivatives, are suitable for use in the preparations according to the present invention. Examples of such cyclosporins are described in, e.g., German Offenlegungsschriften Nos. DE-OS 40,03,844 and DE-OS 40,05,190. Cyclosporin A is preferred.

The active ingredient concentrations in the solutions concentrates according to the present invention are in the range of 20 to 200 mg/mL and preferably 50 to 100 mg/mL.

The alcohol components are monohydric and/or polyhydric alcohols used as individual substances or in random mixtures, e.g., ethanol, propylene glycol and/or polyethylene glycols with a molecular weight of up to 600. Ethanol and/or propylene glycol are preferably used.

In addition, the preparations according to the present invention may optionally also contain other carrier and/or auxiliary substances suitable for intravenous administration, and the preparations intended for oral administration may contain usual pharmaceutical additives, e.g., taste-improving agents, diluents, preservatives, isotonizing agents, etc.

The present invention is explained in greater detail by the following examples, without being limited to them.

EXAMPLE 1

Seventy g of polyoxyethylene glycerol monooleate (Tagat O) were mixed with 30 g of propylene glycol. Five g of cyclosporin A were dissolved in the resulting mixture at room temperature. The volume of the solution was increased to 100 mL with propylene glycol, and was homogenized by stirring. Depending on the intended use, the solution thus prepared was put into bottles or ampules, or subjected to further processing into soft gelatin capsules. For parenteral preparations, the preparation and the filling must be performed under sterile conditions. The active ingredient concentration is adjusted to the desired content by dilution with water or aqueous solutions before therapeutic use.

EXAMPLE 2

Eighty g of polyoxyethylene glycerol monolaurate (Tagat L2) were mixed with 10 g of 96-vol. % ethanol. Five g of cyclosporin A were dissolved in this solution at room temperature while stirring. The solution thus obtained was made up to 100 mL with 96-vol. % ethanol, and it was homogenized by stirring. Further processing is as described in Example 1.

EXAMPLE 3

Thirty g of polyoxyethylene glycerol monolaurate (Tagat L2) were mixed with 65 g of propylene glycol. Five g of cyclosporin A were dissolved in this mixture.

The preparation thus obtained was subjected to further processing as described in Example 1.

EXAMPLE 4

Seventy g of polyoxyethylene glycerol monostearate (Tagat S) were mixed with 30 g of 96-vol. % ethanol, and 5 g of cyclosporin A were dissolved in this [mixture] while stirring. The preparation thus obtained was subjected to further processing as in Example 1.

EXAMPLE 5

Seventy-five g of polyoxyethylene glycerol monostearate (Tagat S) were mixed with 10 g of 96-vol. % ethanol and 10 g of propylene glycol, and 5 g of cyclosporin A were dissolved in this mixture while stirring. The solution was made up to 100 mL with 96-vol. % ethanol, and it was homogenized by stirring. Further processing is as described in Example 1.

EXAMPLE 6

Sixty g of polyoxyethylene glycerol monooleate (Tagat O) were mixed with 20 g of 96-vol. % ethanol, and 5 g of cyclosporin A were dissolved in this [mixture] while stirring. The solution was made up to 100 mL with 96-vol. % ethanol. Further processing is as described in Example 1.

EXAMPLE 7

Eighty-eight g of polyoxyethylene glycerol monooleate (Tagat O) were mixed with 10 g of propylene glycol, and 10 g of cyclosporin A were dissolved in this mixture while stirring. The solution was made up to 100 mL with propylene glycol, and it was subjected to further processing as described in Example 1.

The solution concentrate prepared according to the present invention are filled into bottles or ampules, and they are diluted to the desired active ingredient content before the therapeutic use. Depending on the desired active ingredient content, the solution and concentrate are diluted at weight ratios ranging from 1:10 to 1:100. Water or aqueous solutions, e.g., physiological saline solutions, glucose, dextran, fructose, or mannitol solutions, may be used as the diluents.

Solution concentrate for oral administration may also be filled into soft gelatin capsules.

The preparations according to the present invention showed no precipitation, decomposition or other changes after storage for 6 months at temperatures ranging from −18° C. to 60° C. (stress test).

Bioavailability

A group of beagle dogs was used for the bioavailability studies on the compositions according to the present invention. The preparations to be tested were administered orally to fasting animals by means of a stomach tube. Blood was taken from the saphenous veins of the animals at defined time intervals, and were collected in corresponding plastic tubes with added EDTA. The blood samples were stored at −18° C. until time for the determination. Cyclosporin was determined in the whole blood by fluorescence polarization immunoassay (FPIA).

The areas under the curves (AUC), on which the concentrations of the drug in the blood were plotted as a function of time, were calculated according to the trapezoidal rule. The average AUC values of the composition according to the present invention are substantially higher than those of the commercially available Sandimmun drinking solution, which were determined in the same manner, at the same dosage, in the same dogs. The data from the curve is set forth in Table I.

TABLE I

| Sample | AUC (0–12 h) ng/ml |
|---|---|
| 1 | 13.600 ± 1.542 |
| 2 | 10.277 ± 2.196 |
| 4 | 12.092 ± 3.128 |
| 5 | 12.153 ± 2.352 |
| Cyclosporin Drinking Solution | 7.452 ± 2.452 |

From Table I it is apparent the preparations according to the invention yield a higher degree of bioavailability for cyclosporin than cyclosporin in a known drinking solution.

Depending on the composition, the bioavailabilities of the pharmaceutical preparations according to the present invention are surprisingly, i.e. 40 to 70%, higher than that of the formulation that is currently commercially available.

Due to this surprising result, it is possible to reduce the dose of the active ingredient and thus to drastically reduce the severe side effects of the currently available formulations, especially the nephrotoxic side effects.

Having thus described our invention, what is desired to be secured by Letters Patent of the United States is set forth in the appended claims.

We claim:

1. A liquid pharmaceutical composition for oral or parenteral administration, comprising cyclosporin as the active ingredient in combination with a polyoxyethylene glycerol fatty acid monoester selected from the group consisting of monoesters of lauric, stearic, oleic or isostearic acid, and an alcohol selected from the group consisting of monohydric, polyhydric or mixtures thereof, selected from the group consisting of ethanol, propylene glycol, polyethylene glycol with a molecular weight of up to about 600, and mixtures thereof.

2. A liquid pharmaceutical composition in accordance with claim 1, wherein said polyoxyethylene glycerol fatty acid monoester is a monoester of oleic or lauric acid.

3. A pharmaceutical composition in accordance with claim 1, wherein the cyclosporin is cyclosporin "A".

4. A pharmaceutical composition in accordance with claim 1, wherein the cyclosporin polyoxethylene glycerol fatty acid monoester to alcohol ratio is in the range 1:1–20:0.5–20.

5. A pharmaceutical composition in accordance with claim 4, wherein said ratio is in the range 1:10–20:2–10.

6. A pharmaceutical composition in accordance with claim 4, wherein said ratio is in the range 1:12–18:3–6.

7. A pharmaceutical composition in accordance with claim 1 wherein cyclosporin is present in a concentration of between 20 and 200 mg/mL.

8. A pharmaceutical composition in accordance with claim 7, where cyclosporin is present in a concentration of between 50 and 100 mg/mL.

9. A method of preparing a pharmaceutical composition for oral on parenteral administration by mixing, at a temperature of from 20° to 50° C., cyclosporin with a polyoxyethylene glycerol fatty acid monoester selected from the group consisting of monoesters of lauric, stearic, oleic or isostearic acid, and an alcohol selected from the group consisting of monohydric, polyhydric or mixtures thereof, selected from the group consisting of ethanol, propylene glycol, polyethylene glycol with a molecular weight of up to about 600 and mixtures thereof so that the ratio of cyclosporin to polyoxyethylene glycerol fatty acid monoester to alcohol is in the range of 1:1–20:0.5–20 and filling suitable containers with said composition.

10. A method in accordance with claim 9, wherein the ratio range is 1:10–20:2–10.

11. A method in accordance with claim 9, wherein the ratio range is 1:12–18:3–6.

12. A method of preparing a pharmaceutical composition for oral or parenteral administration by mixing, at a temperature of from 20 to 50° C., cyclosporin with a polyoxyethylene glycerol fatty acid monoester selected from the group consisting of monoesters of lauric, stearic, oleic or isostearic acid, and an alcohol selected from the group consisting of monohydric, polyhydric or mixtures thereof, selected from the group consisting of ethanol, propylene glycol, polyethylene glycol with a molecular weight of up to about 600 and mixtures thereof so that the cyclosporin is present in a concentration of from 20 to 200 mg/mL and filling suitable containers with said composition.

13. A method in accordance with claim 12, wherein the concentration of cyclosporin is from 50 to 100 mg/mL.

* * * * *